Oct. 27, 1936. B. A. BOURNE Plant Pat. 203
SUGAR CANE
Filed May 11, 1936
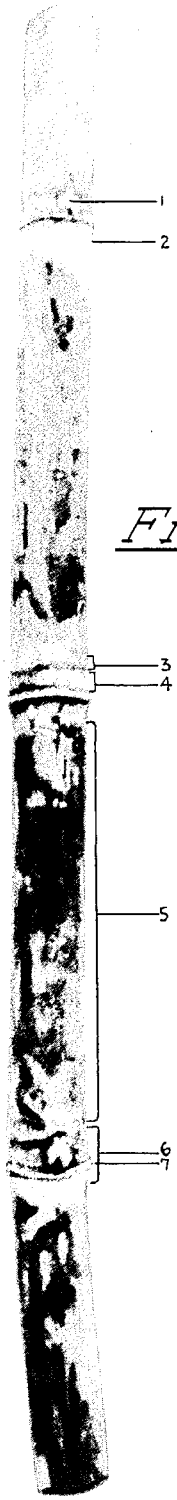
Fig. I
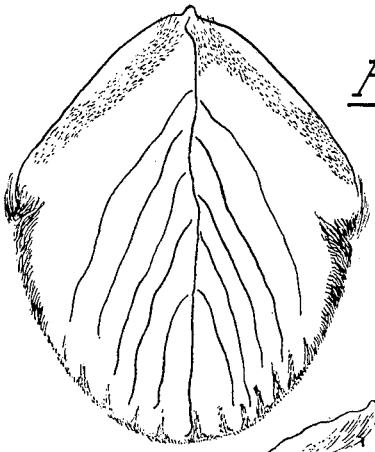
Fig. III
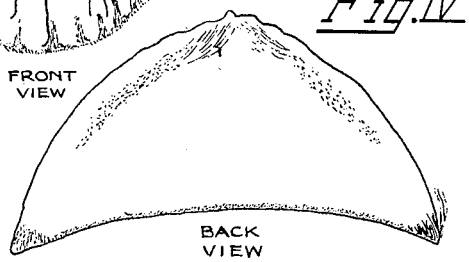
Fig. IV
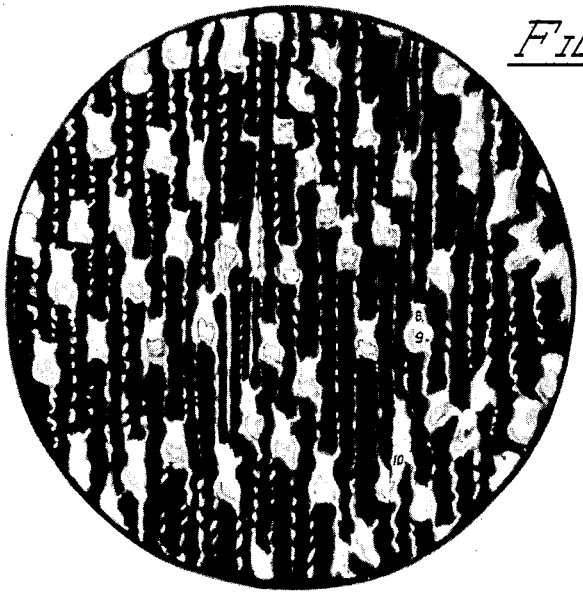
Fig. II
INVENTOR
Benjamin Arthur Bourne
By Orville M. Kile
PLANT PATENT AGENT Patented Oct. 27, 1936

Plant Pat. 203

UNITED STATES PATENT OFFICE

203

SUGAR CANE

Benjamin Arthur Bourne, Clewiston, Fla.

Application May 11, 1936, Serial No. 79,159

1 Claim. (Cl. 47—59)

My new variety originated as a seedling and is the result of definite breeding efforts carried on by me. The crossing of the immediate ancestors of this variety was done by me in December, 1931, at Lake Harbor, Florida. This cross was between two unnamed but numbered seedlings, one of which was in turn originated by myself through a cross made several years earlier. The parentage goes back to Louisiana Purple and Chunnee, through several intervening generations.

This variety is an excellent and rapid germinator, producing primary shoots early in growth. It does not have the objectionable character of producing "suckers" late in the season which would result in immature stalks at harvest time.

This is a very early maturing variety. When planted in the Everglades of Florida during the fall or early winter, it will by the middle of the following October give satisfactory yields of cane sugar (sucrose) amounting to from 8 to 10 percent by weight of the cane. If not harvested in the fall (or about a year from the date of planting, if same was done in the fall) it will gradually increase in sugar (sucrose) content for from 4 to 5 months, reaching a maximum of from 13 to 17 percent cane sugar (by weight of the cane), depending on soil and weather conditions.

This variety is very resistant to mosaic and leaf diseases due to species of *Helminthosporium*. Also it is very resistant to red-rot of the stalk and to wind damage. The very strong root system which it possesses prevents uprooting of stools under severe weather conditions.

The original illustration shows; Fig. I—a mid-section of a typical stalk showing the variety of colors, Fig. II—typical structure of stem epidermis magnified by 295, and Figs. III and IV—the front and back views of a typical stem bud.

The following is a detailed description of my new variety of sugar cane.

*The stalk*

*Structure.*—Stalks are very solid in cross section and are very hard. As compared with other sugar canes they are medium to high in fiber content.

*Growth.*—Stalks are erect from the start and remain upright throughout the growth cycle. They may attain a height of from 7 to 10 feet or more, depending upon soil type, weather conditions and period of growth.

*Size.*—Diameter of stalk as measured from the middles of 50 stalks selected at random, varied from 1.90 centimeters to 2.83 centimeters, averaging 2.37 cms.

*Internodes* (Fig. I—5).—In middle of stalk frequently reach a length of 12.5 centimeters and follow one another in almost a straight line, being only very slightly "staggered".

*Nodes.*—Approximately the same in diameter as the internode portion, no constriction being observed. (Fig. I—6.)

*Color.*—Very variable. At the base of mature stalks it is greenish or brownish-green, but on passing to the middle and top portions it shows shades of yellow-brown, purple-brown and light purple. Typical colors and markings on middle stalk portions are shown in Fig. I.

*Furrows* (or eye grooves immediately above the eyes).—Usually absent, but occasionally a very slight furrow is present (Fig. I—above 1).

*Wax or "bloom".*—Abundant on the surface of the stem, but sometimes falls off the lower and older portions at maturity. There is always a distinct "wax ring" below the node (Fig. I—2).

*Root band.*—Color is usually green; shape is oblique. Root "eyes" frequently have purplish centers. Eyes are placed irregularly in one or two rows (Fig. I—4).

*Growth ring.*—Color green at first, but turns a purple-brown with age and sunlight. Shape is elevated (Fig. I—3).

*Rind.*—Splitting or cracking of the rind has not been known to occur.

*Leaf scar.*—Prominent (Fig. I—7).

*Leaves*

*Blade.*—Dark green in color; width 4.2 to 4.4 centimeters across widest portion of mature outer blades. Grows somewhat upright but with top overhanging.

*Leaf sheath.*—Sides, upper and lower portions glabrous, but about midway between base and top there are present sharp hairs in a patch about 2 inches by one-half inch. Old sheaths drop sharp hairs and are usually entirely smooth.

*Throat.*—Coated with felted hairs.

*Collar.*—Shows the triangular areas meeting midrib, but not coalescing. Surface waxy.

*Ligule.*—0.5 centimeter long. Edge fimbriate.

*Leaf stripping.*—The dead leaves and leaf-sheaths usually fall away readily from the stalk at maturity.

*Stem buds*

*Size.*—Good, ranging from 0.9 to 1.1 centimeters wide by 0.9 to 1.2 centimeters long.

*Position.*—Not prominent; that is, they do not protrude much from the surface of the stalk. Thus in handling the cane for planting purposes, little bud damage occurs. The tip of the bud does not reach above the growth ring (Fig. I—1 and 3) and the base is very close to the base of the leaf sheath.

*Form.*—For typical form and hair groups, see Figs. III and IV, showing both front and back views.

*Stem epidermal cells*

The average width of epidermal cells is approximately 12.2 microns, which is considered wide for sugar cane commercial varieties. The number of short-cell groups (Fig. II—3 and 9) per square millimeter is characteristically low, being only about 600. The number of stomata per microscopic circular field of 1.9 square millimeters varies usually between 2 and 3. Pointed, elongated cork cells (Fig. II—10) are scarce. Solitary cork cells (Fig. II—9 is the cork cell and 1 the silica cell attached) are very rarely found. Solitary silica cells have never been observed.

*Inflorescence*

This variety does not bloom readily. If it blooms at all, it does so late in the flowering season, or during late February or early March in southern Florida.

Male anthers have never been observed to have fertile pollen.

Stigmas are deep purple and apparently normal.

Ovaries are plump and apparently normal.

The principal characteristics which in combination help to distinguish my new variety from all other known varieties of sugar cane are:

1. Very much earlier maturity.
2. Different color and shape of (*a*) stalk and (*b*) bud.
3. Different pattern of stem epidermis.
4. Upright growth habit of leaves and stalks.
5. High sugar-producing ability on raw everglades peat soils.
6. Resistance to diseases common to sugar canes.
7. Strength of root system.
8. Absence of splitting of rind.
9. Solidity of stalk.
10. Rapidity of germination without producing late "suckers".

Having thus disclosed my invention, what I claim as new is:

The variety of sugar cane herein shown and described, characterized particularly by its early maturity, resistance to disease, high sugar-content, distinctive color and shape of stalk and bud, distinctive pattern of stem epidermis, and its strong upright growth.

BENJAMIN ARTHUR BOURNE.